United States Patent
Roberts et al.

(10) Patent No.: US 9,155,809 B2
(45) Date of Patent: Oct. 13, 2015

(54) PEN STERILIZATION DEVICE

(76) Inventors: Michael Roberts, St. Cloud, FL (US); John Michael Roberts, St. Cloud, FL (US); Lucas Todd Roberts, St. Cloud, FL (US)

(*) Notice: Subject to any disclaimer, the term of this patent is extended or adjusted under 35 U.S.C. 154(b) by 961 days.

(21) Appl. No.: 13/249,633

(22) Filed: Sep. 30, 2011

(65) Prior Publication Data
US 2013/0081660 A1  Apr. 4, 2013

(51) Int. Cl.
*A61L 2/18* (2006.01)

(52) U.S. Cl.
CPC .............. *A61L 2/18* (2013.01); *A61L 2202/121* (2013.01); *A61L 2202/122* (2013.01)

(58) Field of Classification Search
CPC ....... A61L 2/00; A61L 2/18; A61L 2202/121; A47L 25/00; C11D 3/48; C11D 3/50
USPC ...................... 15/104.94, 104.92, 220.4, 423; 422/300, 28, 292
See application file for complete search history.

(56) References Cited

U.S. PATENT DOCUMENTS

| | | | | |
|---|---|---|---|---|
| 5,308,406 | A | * | 5/1994 | Wallock et al. .................. 134/42 |
| 5,683,655 | A | * | 11/1997 | Carter .............................. 422/28 |
| 5,731,282 | A | * | 3/1998 | Duquesne ..................... 510/423 |
| 6,269,512 | B1 | * | 8/2001 | Thomson et al. .......... 15/104.92 |
| 2003/0217423 | A1 | * | 11/2003 | Larsen ....................... 15/104.92 |
| 2010/0322699 | A1 | | 12/2010 | Dam |
| 2011/0146012 | A1 | * | 6/2011 | Hirst .......................... 15/104.93 |

* cited by examiner

*Primary Examiner* — David Cormier
*Assistant Examiner* — Irina Graf
(74) *Attorney, Agent, or Firm* — Jason T. Daniel, Esq.; Daniel Law Office, P.A.

(57) ABSTRACT

A pen sterilization device includes a main body having a first end, a second end and a plurality of opposing sides defining a watertight reservoir for containing a sterilization agent. A pair of watertight valves are positioned along each end of the main body and function to allow ingress and egress of a pen to be cleaned. A central partition may be provided within the watertight reservoir having one or more brushes that are suspended in the sterilization agent for scrubbing a pen that is passing through the device.

11 Claims, 8 Drawing Sheets

PEN STERILIZATION DEVICE

BACKGROUND

Field of the Invention

The present invention relates generally to sanitation devices, and more particularly to a pen sterilization device capable of quickly and easily sterilizing writing instruments and other such devices before and after each use.

Each year, thousands of people become sick or die after contracting a disease or infection. In many cases, victims are exposed to disease carrying bacteria, germs and viruses, after touching objects such as pens which are rarely, if ever, sanitized. This is particularly problematic in locations such as schools, hospitals, doctor's offices and nursing centers, for example, that are frequented by persons with weakened immune systems.

There are many known methodologies directed towards preventing the spread of contagions. One method commonly employed by hospitals and other public locations includes the use of sprays that sanitize common areas. However these sprays can only clean surface areas onto which the solution makes contact. As a result, it is impossible to fully clean all sides of small items such as pens and pencils, for example, which are handled by many different people throughout the course of a day.

There have been previous devices directed towards cleaning small objects. One recent example described in U.S. Patent Publication No. 2010/0322699, utilizes a sponge that is soaked with a sanitizing agent to clean items. However, the '699 disclosure suffers from the fact that the device is generally open to the outside air which causes the solution to quickly evaporate. Additionally, the '699 document discloses the use of a sponge to clean objects, but only those objects having a surface area that can make physical contact with the sponge can be cleaned by the solution. Moreover, laboratory tests have shown that porous materials, such as sponges will retain contagions when utilized repeatedly over long periods of time.

Accordingly, there remains a need for a device capable of quickly, easily and repeatedly cleaning pens and other writing instruments that does not suffer from the drawbacks of the devices described above.

SUMMARY OF THE INVENTION

The present invention is directed to a pen sterilization device. One embodiment of the present invention can include a main body having a first end, a second end and a plurality of opposing sides defining a watertight reservoir for containing a sterilization agent. A pair of watertight valves can be located within the first and second ends for maintaining a watertight seal while allowing ingress and egress of a pen.

Another embodiment of the present invention can include a central partition having a plurality of brushes for cleaning the pen.

Yet another embodiment of the present invention can include a central partition having another valve for creating two separate chambers within the reservoir. Each of these chambers can contain the same or different solutions.

Yet another embodiment of the present invention can include one or more drip channels disposed within the reservoir for removing any excess solution from the pen.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Figure 1:
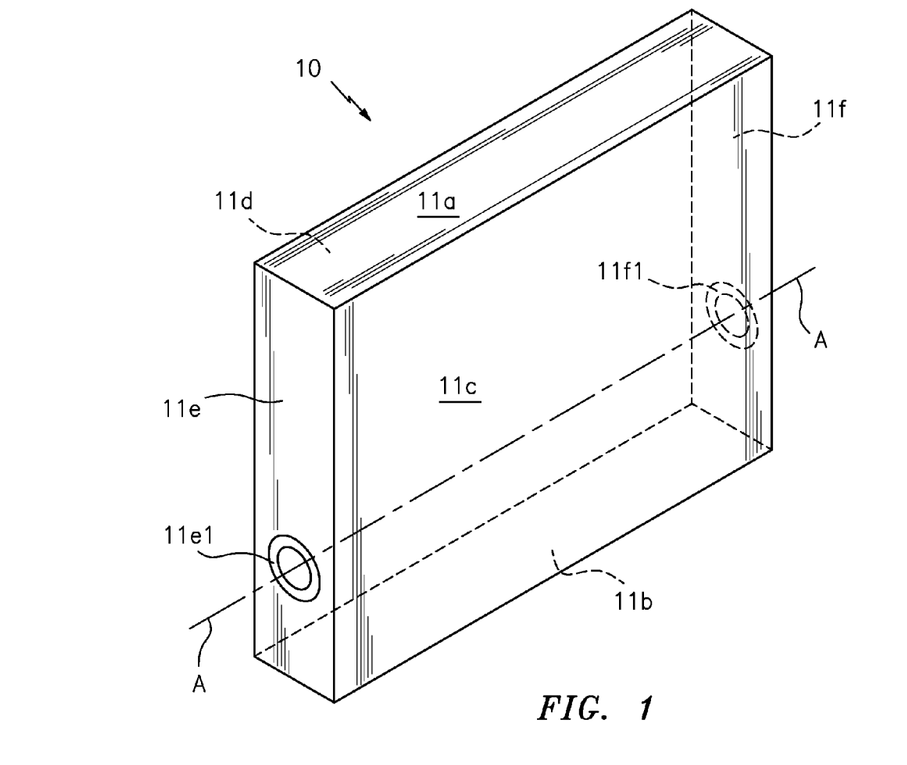
FIG. 1 is a perspective view of a pen sterilization device that is useful for understanding the inventive concepts disclosed herein.

For purposes of this description, the terms "upper," "bottom," "right," "left," "front," "vertical," "horizontal," and derivatives thereof shall relate to the invention as oriented in FIG. 1. Although described throughout this document as a device for sterilizing pens, one of skill in the art will recognize that other items such as pencils, stylus devices, pointers and the like can also be utilized herein. Additionally, one of skill in the art will recognize that the inventive concepts disclosed herein can be utilized to sterilize other objects with minimal alterations to the disclosed device. Accordingly, the invention is not limited to the illustrated embodiments.

FIG. 1 illustrates one embodiment of a pen sterilization device 10 that is useful for understanding the inventive concepts disclosed herein. To this end, the device can act to quickly and effectively sanitize all surfaces of writing instruments, such as pens, for example, by introducing the pen to a sanitizing agent prior to, and/or after each use. Additionally, by constructing the below described components into a relatively small device, it becomes possible to position the device on desktops or other locations where writing instruments are commonly found.

As shown, the pen sterilization device 10, according to one embodiment, can include a main body 11, a pair of self sealing valves 12, and a sanitizing solution 13.

The main body 11 can act as a vessel for securely positioning the valves 12 and solution 13 in a watertight manner. In one embodiment, the main body 11 can include a generally rectangular shape having a top surface 11a, a bottom surface 11b, a front surface 11c a back surface 11d and a pair of side surfaces 11e and 11f, which act in unison to form a cavernous interior space that forms a watertight reservoir for containing a solution. As shown, side surfaces 11e and 11f can further include openings 11e1 and 11f1, respectively positioned along a horizontal axis A.

In one preferred embodiment, main body 11 can be constructed from transparent sheets of acrylic, acetate or plastic that are joined together in a conventional manner. Of course, other known materials and manufacturing processes such as injection molded plastic, and composite materials, for example are also contemplated.

Figure 2:
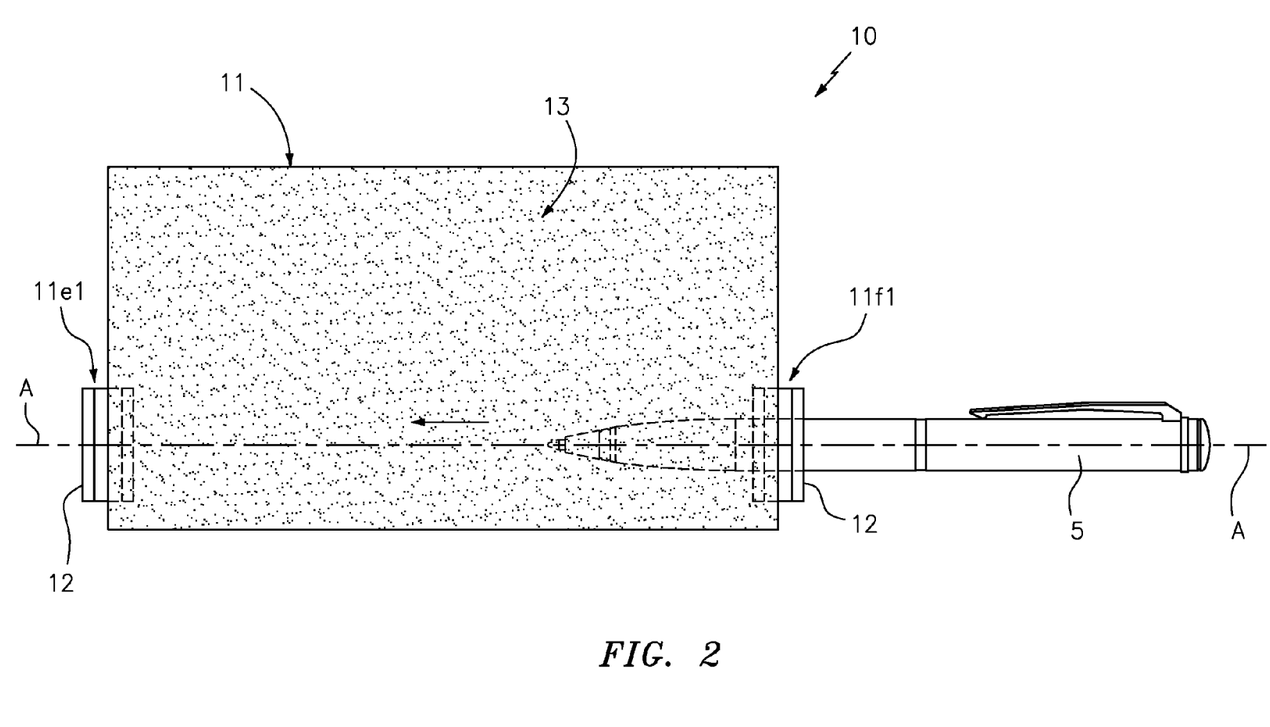
FIG. 2 is a side view of a pen sterilization device in use according to one embodiment of the invention.

As shown in FIG. 2, a pair of two-way self sealing valves 12 can be positioned within the openings 11e1 and 11f1, along the horizontal axis A, so as to be arranged in a linear manner. As described herein, valves 12 can include any number of known devices capable of maintaining a watertight seal for retaining the solution 13 within the main body 11, and allowing a pen 5 to be slid through the reservoir in any direction (i.e. forward or backward relative to axis A). Non-limiting examples of a suitable valve can include a conventional duckbill valve, an insulin-type self sealing tube, or a butyl rubber stopper, among many others.

Solution 13 can act to instantaneously kill contagions such as bacteria, germs and viruses, among others. In one embodiment solution can be a liquid, and in other embodiments the solution 13 can take the form of a gel. In either instance, solution 13 can include a sterilization agent and can be positioned within the main body/reservoir 11 so as to engulf the entire surface area of a pen that traverses through the device via the opposing valves 12.

Sterilization agents are well known in the art and typically include one or more active ingredients such as isopropanol, ethanol, n-propanol, or povidone-iodine, as well as inactive ingredients such as polyacrylic acid, humectants, propylene glycol, for example.

Figure 3:
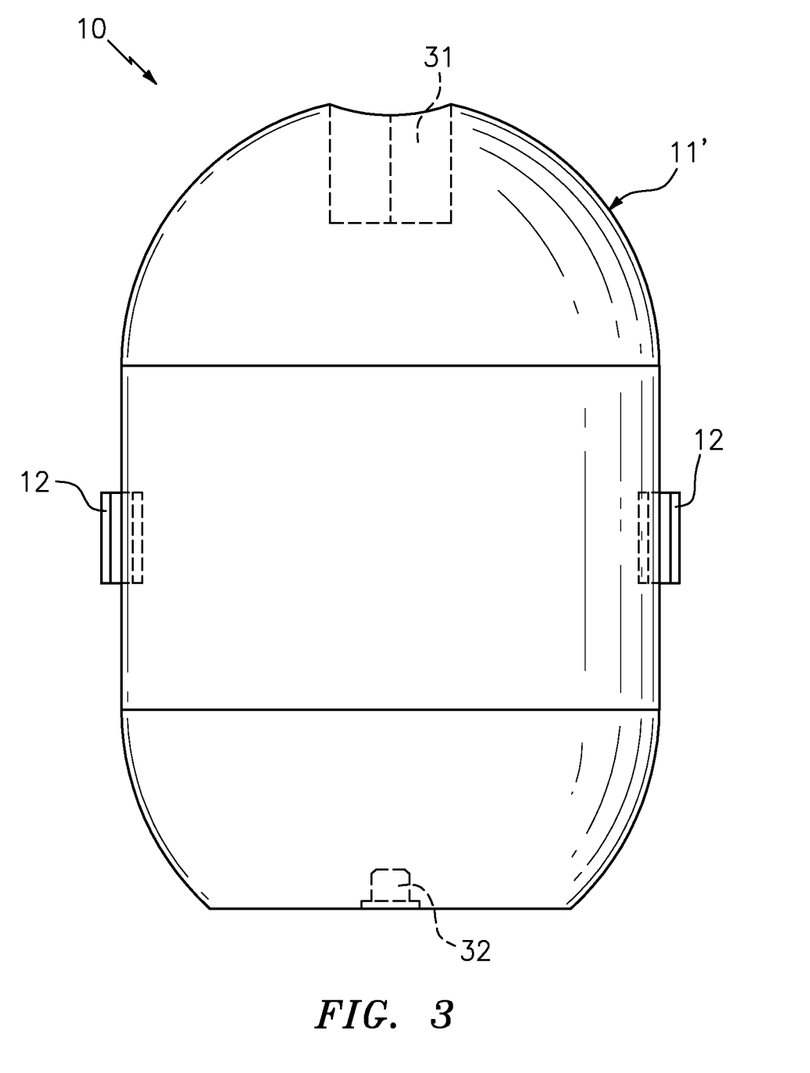
FIG. 3 is a frontal view of an alternate embodiment of the present invention.

As described above, the main body 11 can take any number of different shapes and sizes. Accordingly, FIG. 3 illustrates an alternate embodiment of a pen sterilization device 10 that includes a generally egg shaped main body 11' and further includes optional components such as one or more pen holders 31 and a plug 32 for refilling the solution 13 as needed.

Figure 4:
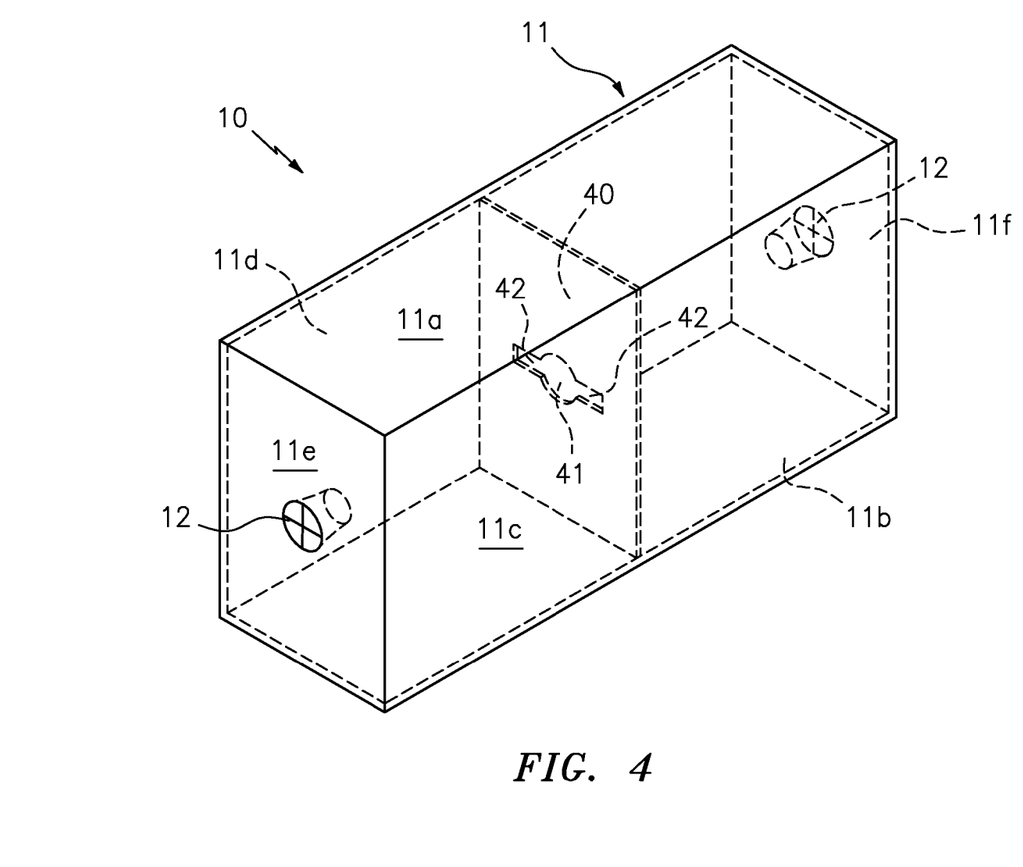
FIG. 4 is a top perspective view of another embodiment of the present invention.

FIG. 4 illustrates a top view of a pen sterilization device 10 that further includes a partition 40. As shown, the partition 40, according to one embodiment can be located in the middle of the reservoir/main body area at a location approximately half way between side walls 11e and 11f along the horizontal axis A. Partition 40 can therefore be secured to the main body along the top 11a, bottom 11b front 11c and back 11d surfaces. As described herein, partition 40 can be virtually identical to either of the side portions 11e and 11f in both construction materials and dimensions, and can further include openings 41 and/or 42.

In one embodiment, opening 41 can be virtually identical to openings 11e1 and 11f1 described above, so as to be aligned with valves 12 for allowing a pen 5 to pass through the entire device without encountering any obstacles. As will be described below, openings 42 can include any number of different shapes and sizes for positioning additional components such as the cleaning brushes 50 described below.

Figure 5:
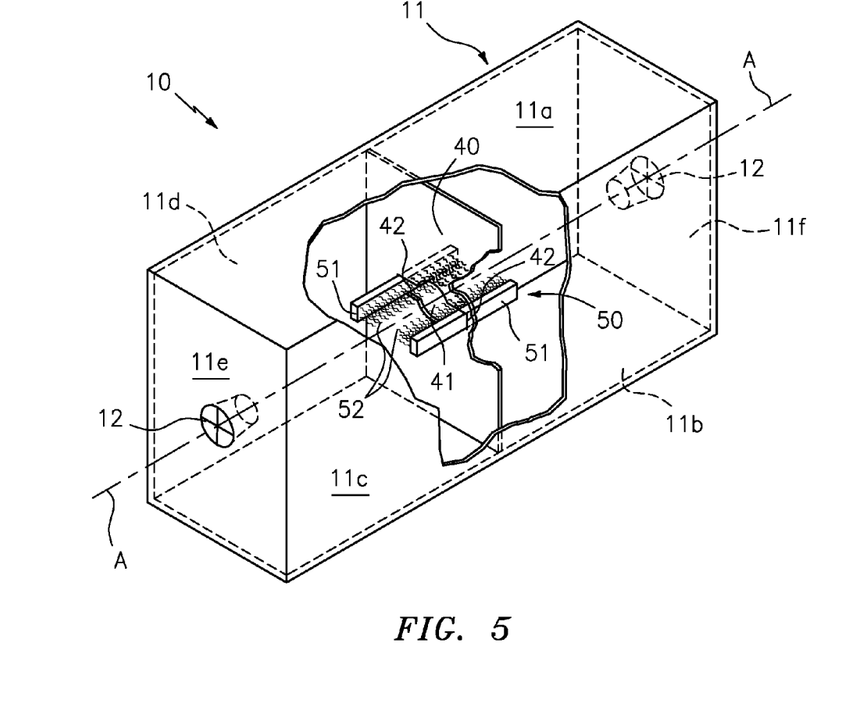
FIG. 5 is a top perspective view of another embodiment of the present invention.

FIG. 5 illustrates another embodiment of a pen sterilization device 10 that further includes one or more brushes 50 having brush pads 51 and a plurality of cleaning bristles 52 extending therefrom. As shown, the brush pads 51, according to one embodiment can include a generally rectangular shape that is positioned within opening 42 of the partition 40, or can be conventionally secured to the partition 40 itself. The brush pads 51 can orient the bristles 52 so as to be in line with opening 41. In this configuration, whenever a pen 5 is inserted through the device 10 along axis A, the pen will pass through the opening 41 at which time the bristles 52 can act to remove any debris from the pen, thus increasing the effectiveness of the solution 13 located therein.

In one preferred embodiment, the brush pad 51 can be constructed from wood, plastic or PVC that is secured to the partition 40 and opening 42 via conventional hardware such as glue, screws, adhesive material and others. Additionally, the plurality of bristles can include elongated strands of soft plastic, rubber or fabric, among other materials that are secured to the brush pad in a conventional manner. Moreover, although illustrated as including two brushes, one of skill in the art will recognize that any number of brushes can be secured to the partition or other internal locations of the reservoir. Accordingly, the device is not limited to the specific embodiment shown above.

Figure 6:
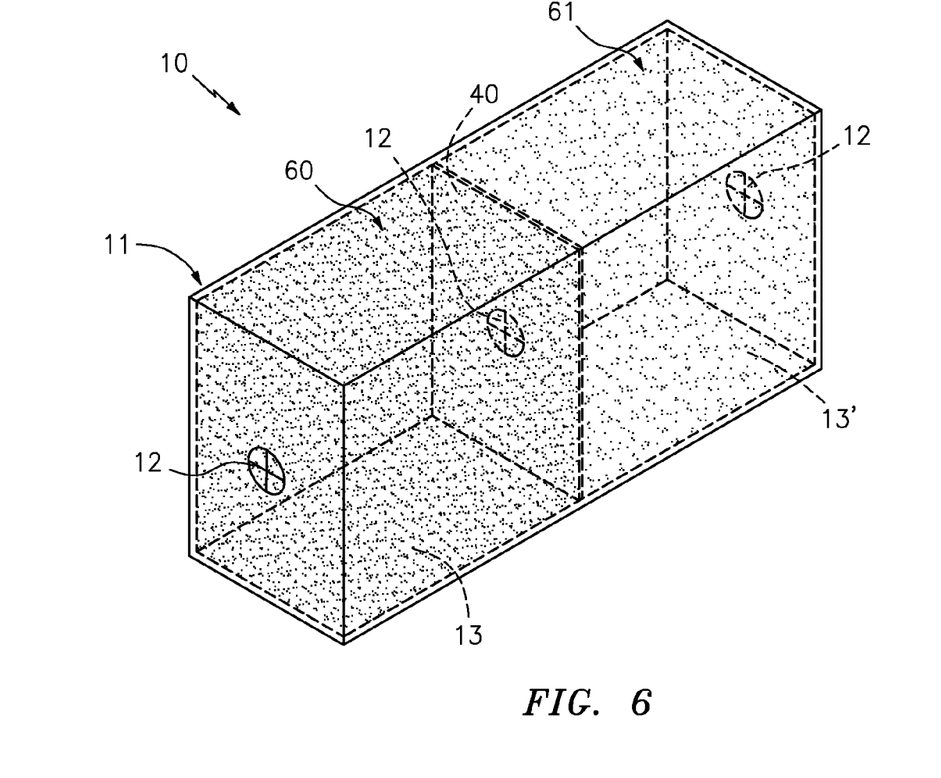
FIG. 6 is a top perspective view of an alternate embodiment of the present invention.

FIG. 6 illustrates another alternate embodiment of a pen sterilization device 10 that further includes another valve 12 that is secured within the opening of the partition 40 so as to create two internal waterproof chambers 60 and 61 within the main body. Note that opening 42 is not present in this embodiment. By providing a self sealing waterproof valve 12, as described above onto the partition 40, it becomes possible for the device 10 to contain two different solutions 13 and 13'.

As described herein, solution 13' can be the same as solution 13 described above, or can include different materials directed towards a different objective. For example, solution 13' can include an aromatic agent such as lemon extract, for example, designed to remove any unpleasant odors that may be imparted onto the pen from the sterilization solution 13 described above. Alternatively, solutions 13 and 13' can each be directed towards different forms of sterilization agents designed to specifically target certain contagions. For example, solution 13 can include sterilization agents directed specifically to combating viruses, whereas solution 13' can include sterilization agents directed specifically towards killing bacteria. Of course, other embodiments having different purposes and materials are also contemplated.

Figure 7:
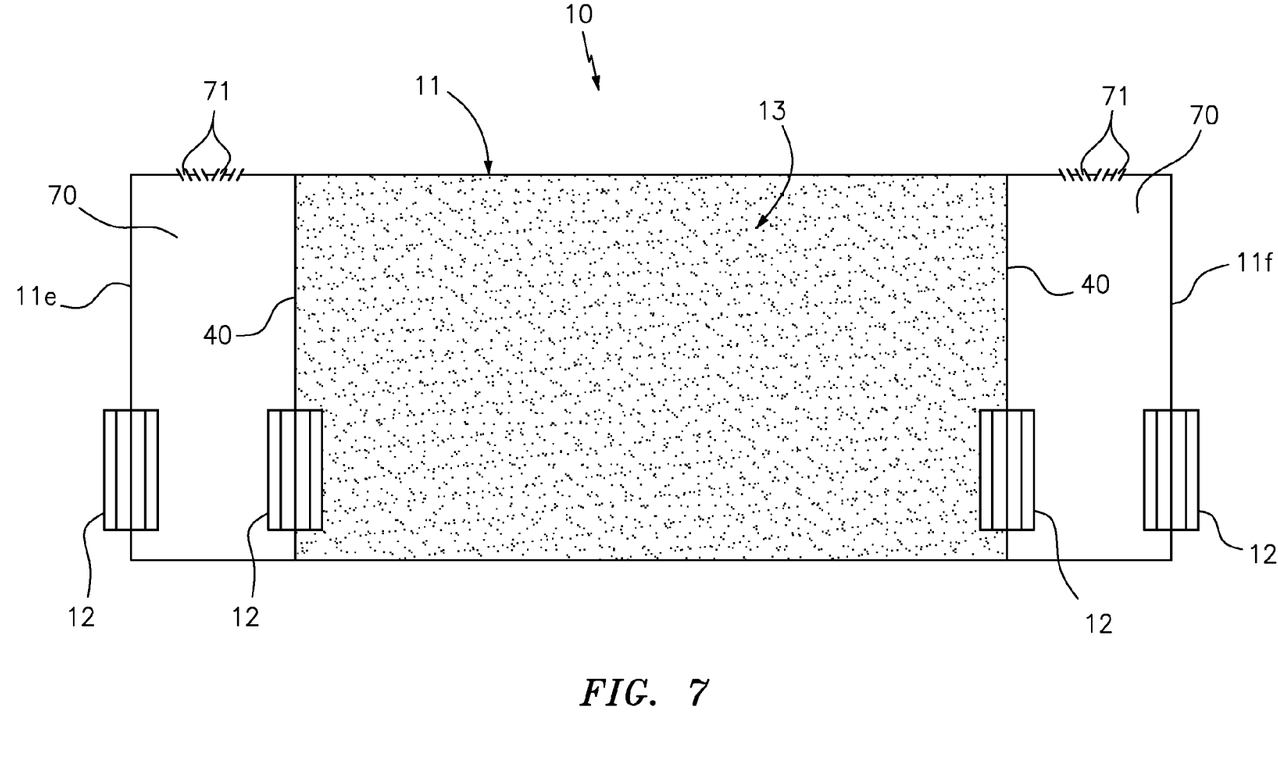
FIG. 7 is a side view of another alternate embodiment of a pen sterilization device.

FIG. 7 illustrates another alternate embodiment of a pen sterilization device 10 that further includes a pair of drip channels 70 located adjacent to each of the side walls 11e and 11f. As shown, each of the drip channels can be formed at a time of manufacture by securing a partition 40 having an integrated valve 12 adjacent to each of the side walls 11e and 11f, respectively within the main body. As described above, by placing a partition and valve within the main body, it becomes possible to create a watertight compartment. In the present embodiment, the pair of partitions act to create two chambers interposed between the center of the main body and the side walls.

In operation, the central portion (i.e. reservoir) of the main body can contain the solution 13 and the drip channels 70 will be dry. Accordingly, whenever a pen is slid through the device, the pen will become wet from the contact with the solution 13, and the drip channels 70 will act to collect any remaining solution from the pen before it exits the device, regardless of which direction the pen is pulled/pushed through. Further, each drip channel 70 can also include one or more vents/openings 71 configured to allow air to reach the inside of the drip channel. Such a feature can allow any solution 13 that enters the drip channel to evaporate without affecting the remaining solution contained within the reservoir body.

Figure 8:
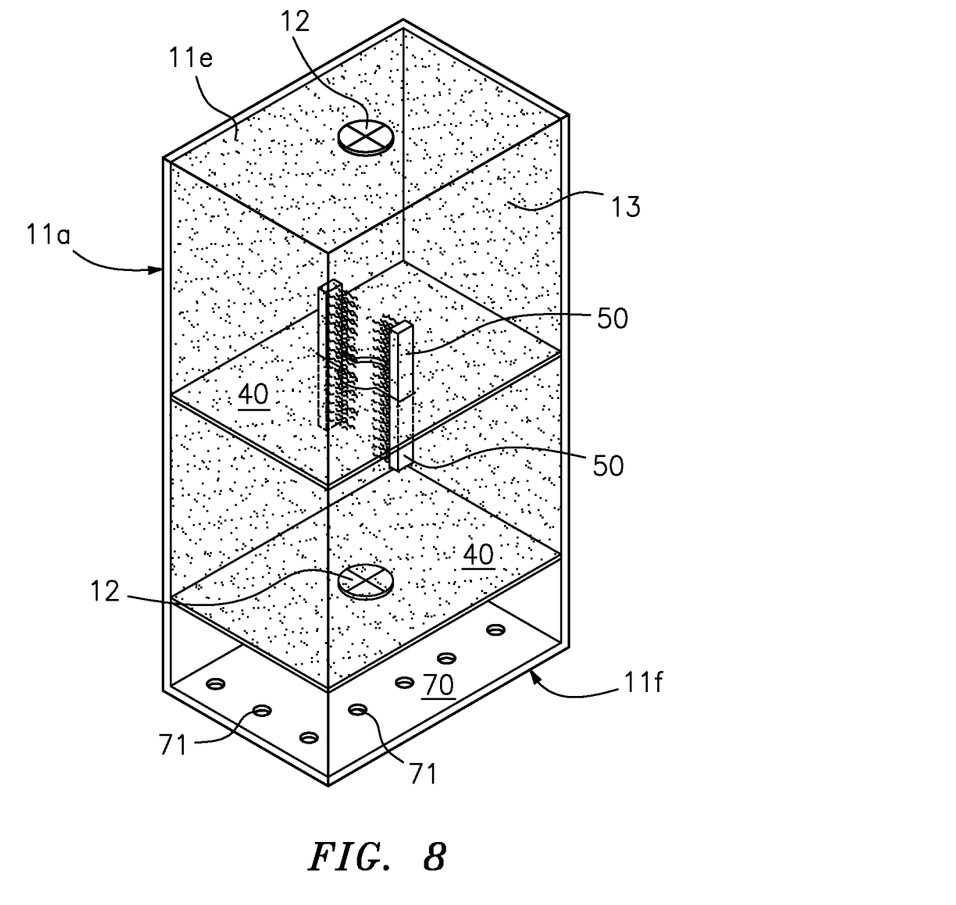
FIG. 8 is a perspective view of a pen sterilization device according to another embodiment of the present invention.

FIG. 8 illustrates another alternate embodiment of a pen sterilization device having a main body 11 that is configured to stand vertically so that side wall 11e, which contains a valve 12, is positioned above side wall 11f. Drip channel 70 (which is constructed via a partition 40, valve 12 and one or more openings 71, as described above) can be positioned adjacent to side wall 11f, and a plurality of brushes 50 can be positioned within the reservoir via a second partition 40. As described above with respect to FIGS. 1-7, each of the valves can be positioned so as to be linear in nature. By providing a vertically oriented device, the above described embodiment can allow a pen to be dipped into the solution and then removed via the same valve, without the need to pull the pen completely through the device. Additionally, such a feature can act to save desk space and require a much smaller footprint while providing the same sterilization activity. Moreover, when a pen is positioned in such a manner, the valve 12 can act to direct the tip of the pen into the drip channel 70, thus allowing the pen tip to remain dry when not in use.

As described herein, one or more elements of the pen sterilization device 10 can be secured together utilizing any number of known attachment means such as, for example, screws, glue, compression fittings and welds, among others. Moreover, although the above embodiments have been described as including separate individual elements, the inventive concepts disclosed herein are not so limiting. To this end, one of skill in the art will recognize that one or more individual elements such as the main body 11, and partition 40 including all subcomponents, for example, may be formed together as one continuous element, either through manufacturing processes, such as welding, casting, or molding, or through the use of a singular piece of material milled or machined with the aforementioned components forming identifiable sections thereof. Accordingly, in one preferred embodiment, each above described element of the pen sterilization device 10 can be constructed from a single form of injection molded plastic having the requisite openings aligned in a precise and linear manner. Of course other materials and construction methodologies are also contemplated.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A pen sterilization device comprising:
   a main body having a first end, a second end, a top end, a bottom end, a front end, and a back end defining a watertight reservoir;
   a solution that is disposed along an entirety of the watertight reservoir;
   a first and second openings disposed within the first and second ends of the main body respectively, said openings being positioned along a horizontal axis;
   a first and second watertight valves located within the first and second openings, respectively, each of said watertight valves functioning to maintain a watertight seal with the watertight reservoir, while allowing ingress and egress of a pen;
   a central partition that is positioned equidistantly from the first and second ends of the main body, said central partition being in communication with each of the top end, the bottom end, the front end and back end of the main body;
   a third opening that is positioned within the central partition along the horizontal axis; and
   one or more generally rectangular brushes that are fully submerged within the solution, and having a plurality of bristles disposed thereon,
   wherein each of the one or more brushes is secured along the third opening, and said bristles are configured to make contact with the pen as it passes through the third opening.

2. The pen sterilization device of claim 1, wherein each of said first and second valves comprises a two-way self sealing valve.

3. The pen sterilization device of claim 1, further comprising:
   a first and second drip channels positioned within the reservoir,
   wherein the first drip channel is located adjacent to an inside portion of the first end,
   the second drip channel is located adjacent to an inside portion of the second end, and
   each of said drip channels are configured to collect excess solution from the pen.

4. The pen sterilization device of claim 3, further comprising:
   a first and second air vents that are disposed along the top end of the main body, said air vents extending into the first and second drip channels, respectively, and functioning to evaporate the solution contained therein.

5. The pen sterilization device of claim 1, wherein the main body is transparent.

6. The pen sterilization device of claim 1, wherein the main body further includes a pen holder.

7. The pen sterilization device of claim 1, wherein the main body further includes a removable drain plug configured to allow a user to deposit and remove the solution from the reservoir.

8. The pen sterilization device of claim 1, wherein the solution includes a sterilization agent that is disposed within the reservoir.

9. A pen sterilization device comprising:
- a main body having a first end, a second end, a top end, a bottom end, a front end, and a back end defining a watertight reservoir;
- a first partition that is disposed within the reservoir at a location adjacent to the first end, and a second partition that is disposed within the reservoir at a location adjacent to the second end;
- each of said first and second partitions being in communication with each of the top end, the bottom end, the front end and back end of the main body to form a first and second drip channel, respectively;
- a solution that is disposed within a central portion of the watertight reservoir that is bounded between the first and second drip channels;
- a first and second air vents that are disposed along the top end of the main body, said air vents extending into the first and second drip channels, respectively, and functioning to evaporate a solution contained therein;
- a first, second, third, and fourth openings disposed within the first end of the main body, the second end of the main body, the first partition and the second partition respectively, said openings being positioned along a horizontal axis; and
- a first, second, third, and fourth watertight valves located within each of the first, second, third and fourth openings, respectively, each of said watertight valves being configured to maintain a watertight seal while allowing ingress and egress of a pen.

10. A pen sterilization device comprising:
- a main body having a first end, a second end, and a plurality of opposing sides defining a watertight reservoir, said main body being configured to stand in a vertical orientation having the first end positioned above the second end, and configured to receive a solution;
- a first partition disposed within the reservoir at a location adjacent to the second end, said partition being in communication with the plurality of opposing sides to form a drip channel;
- a first and second openings disposed within the first end of the main body, and the first partition respectively, said openings being positioned along a linear vertical axis;
- a first and second watertight valves located within the first and second openings, said valves functioning to maintain a watertight seal while allowing ingress and egress of a pen; and
- one or more air vents that are disposed along the main body, each of said one or more air vents extending into the drip channel and functioning to evaporate the solution contained therein.

11. The pen sterilization device of claim 10, further comprising:
- a central partition that is located equidistantly from the first end of the main body and the first partition, said central partition being in communication with the plurality of opposing sides of the main body;
- a third opening that is positioned within the central partition along the linear vertical axis; and
- one or more generally rectangular brushes that are fully submerged within the solution, and having a plurality of bristles disposed thereon,
- wherein each of the one or more brushes is secured along the third opening, and said bristles are configured to make contact with the pen as it passes through the third opening.

* * * * *